(12) United States Patent
Hahnen (10) Patent No.: US 6,270,490 B1
(45) Date of Patent: *Aug. 7, 2001

(54) VENOUS DRAINAGE CATHETER AND METHOD OF USE

(75) Inventor: Kevin Hahnen, San Jose, CA (US)

(73) Assignee: Embol-X, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,314

(22) Filed: Sep. 8, 1998

(51) Int. Cl.[7] ................................................. A61M 31/00
(52) U.S. Cl. .................. 604/509; 604/104; 604/164.03; 604/105; 606/191; 606/194; 606/198
(58) Field of Search ................................. 604/27, 53, 43, 604/19, 28, 48, 500, 73, 93, 173, 264, 523, 164.01–164.03, 509; 606/189, 104, 105

(56) References Cited

U.S. PATENT DOCUMENTS

| | | | |
|---|---|---|---|
| 3,938,530 | * | 2/1976 | Santomieri ........................ 128/349 R |
| 4,808,163 | * | 2/1989 | Laub ..................................... 604/105 |
| 5,112,310 | * | 5/1992 | Grobe ................................... 604/175 |
| 5,415,630 | * | 5/1995 | Gory et al. ............................. 604/53 |
| 5,456,667 | | 10/1995 | Ham et al. ............................ 604/107 |
| 5,618,270 | * | 4/1997 | Orejola ................................. 604/164 |
| 5,637,097 | | 6/1997 | Yoon .................................... 604/174 |
| 5,707,362 | | 1/1998 | Yoon .................................... 604/164 |
| 5,954,745 | | 9/1999 | Gertler et al. ........................ 606/200 |
| 5,984,908 | * | 11/1999 | Davis et al. .......................... 604/282 |

OTHER PUBLICATIONS

Laub, Glenn W. et al., "Novel System for Percutaneous Cardiopulmonary Bypass," *Journal of Investigative Surgery*, vol. 4, No. 2, pp. 217–230, 1991.

Laub et al., "Novel System for Percutaneous Cardiopulmonary Bypass," *Journal of Investigative Surgery*, 4:217–230 (1991).

Takana et al., "Clinical Evaluation of a High–Flow Venous Cannula with Umbrella–Type Basket Tip," Abstract, ASAIO, 44th Annual Conference, New York, NY (Apr. 1998).

* cited by examiner

Primary Examiner—Richard K. Seidel
Assistant Examiner—Jennifer Maynard
(74) Attorney, Agent, or Firm—Lyon & Lyon LLP (57) ABSTRACT

A venous drainage catheter comprising a cannula and a lumen, wherein the proximal end is adapted for attachment to a bypass machine and the distal end has a drainage port in fluid communication with the cannula lumen. Expanding members, having an actuating mechanism which expand the members from a collapsed condition, are disposed circumferentially about the drainage port. Methods for using the devices are also disclosed.

4 Claims, 9 Drawing Sheets

VENOUS DRAINAGE CATHETER AND METHOD OF USE

FIELD OF THE INVENTION

The present invention relates to a venous drainage catheter for drainage of blood from the right atrium, inferior vena cava, or superior vena cava during cardiopulmonary bypass. More particularly, the invention relates to a venous drainage catheter comprising a cannula and expanding members disposed circumferentially about drainage ports for maintaining fluid access to the drainage ports.

BACKGROUND OF THE INVENTION

Cardiopulmonary bypass is commonly used to maintain oxygen delivery to peripheral organs during cardiopulmonary arrest in a variety of cardiothoracic surgeries, septal defect repairs, heart valve repairs and replacement, aneurysm repairs, and corrections of congenital defects. Before cardiopulmonary bypass can be initiated, the heart and coronary blood vessels must be isolated from the peripheral vascular system. This is usually accomplished by arterial cannulation of the aorta and venous cannulation of the right atrium, inferior vena cava, or superior vena cava. Venous drainage catheters are commonly used to withdraw the deoxygenated blood from the right atrium, inferior vena cava, or superior vena cava, pass it to a bypass oxygenator machine, and the blood is thereafter returned to the patient's aorta.

Venous drainage catheters typically include at least one drainage port at the distal end. However, the walls of the organ or vessel within which the drainage ports are disposed will often close down around the drainage ports and thereby obstruct the flow of blood into the cannula. This difficulty will often prevent adequate drainage of blood to the bypass oxygenator machine. Thus, a need exists for an improved venous drainage catheter to prevent obstruction of drainage ports by adjacent tissues during operation.

SUMMARY OF THE INVENTION

The present invention solves these and other problems by providing a venous drainage catheter comprising a cannula having drainage ports at its distal end, and expanding members disposed about the drainage ports. The expanding members serve to keep the organ walls from closing down around the cannula drainage ports. This result is accomplished by providing a larger surface area in the target vessel or organ than is obtainable from conventional catheters or cannulae. This feature promotes flow into the targeted site. This feature of providing a larger surface area also helps to create a venturi effect to facilitate drainage. The expanding members may comprise ribs, fins, mesh, or arms, and generally are embodied as bellows. By use of the present invention, the incision site or the access into the organ is substantially smaller than the expanded diameter of the expanding members.

The present invention relates to a venous drainage catheter comprising a cannula, expanding members, and an actuating mechanism for operating the expanding members. The cannula will generally have a proximal end, a distal end, and a lumen therebetween, the proximal end being shaped for attachment to a bypass oxygenator machine. The distal end will typically include at least one drainage port, or more preferably, a plurality of drainage ports comprising two drainage ports, more preferably three drainage ports, more preferably four drainage ports, more preferably five drainage ports, or more. The drainage ports are in fluid communication with the lumen of the cannula.

The expanding members can be any of ribs, fins, mesh, arms, or bellows. The expanding members are disposed circumferentially about the drainage ports, and may be mounted on the cannula or carried by some other member. The expanding members are capable of expanding from a collapsed condition to a radially expanded condition.

The actuating mechanism for operating the expanding members may include any mechanism that allows deployment of the expanding members by operation from a location proximal the expanding members on the cannula. As but one example of an actuating mechanism, the invention provides a cylindrical sheath disposed circumferentially about the expanding members to maintain the expanding members in a collapsed condition. The sheath is slidable proximally to release the expanding members, where upon the expanding members expand radially outwardly. In certain embodiments of the invention, the sheath will further include a rib mounted at its proximal edge, the rib shaped to engage an incision during use. The rib provides an anchor to stabilize the sheath during advancement of the cannula distally, and may also provide a hemostatic seal to prevent blood loss during use of the venous drainage catheter.

The invention also provides a tubular housing for use in a venous drainage catheter system. The tubular housing includes a proximal end, a distal end, and a lumen therebetween. The lumen is shaped to receive the blood cannula. At a proximal end of the housing, a side opening is provided which communicates with the lumen of the housing and is shaped to allow passage of the cannula through the side opening. The distal end of the housing may have an opening positioned to align longitudinally with the drainage port of the cannula. The expanding members may be disposed circumferentially about the one or more distal openings on the housing, and the expanding members may be mounted on the tubular housing.

The invention also provides methods for draining venous blood from the right atrium of a patient. The surgeon provides a venous drainage catheter as described herein. The surgeon makes an incision in the patient to provide access to the atrial appendage. The cannula, or housing, is inserted through the incision and into the right atrium. The expanding members are activated to the expanded condition to hold tissue away from the drainage port. When a housing is used, the drainage cannula is inserted through the proximal opening of the housing and advanced distally into the atrium. The drainage ports are aligned with a distal opening on the housing. In both methods, the proximal end of the cannula is then attached to a bypass oxygenator machine. Venous blood is then withdrawn from the right atrium and is oxygenated before return to the patient's arterial circulation.

According to the invention, the atrial appendage may be sealed circumferentially about the venous drainage catheter by use of a purse-string suture. In another method, the venous drainage catheter includes the cylindrical sheath disposed about and covering the expanding members to maintain them in a collapsed condition. During use, the cylindrical sheath engages the incision, and is held stable while the cannula is advanced distally, thereby sliding beyond the sheath. By sliding the cannula distally, the expanding members are released inside the right atrium and thereby expand to an expanded condition.

BRIEF DESCRIPTION OF THE DRAWINGS

Reference is now made to a brief description of the drawings, which are intended to illustrate a venous drainage catheter for use herein. The drawings and detailed description which follow are intended to be merely illustrative and are not intended to limit the scope of the invention as set forth in the appended claims.

DETAILED DESCRIPTION OF THE PREFERRED EMBODIMENTS

Figure 1:
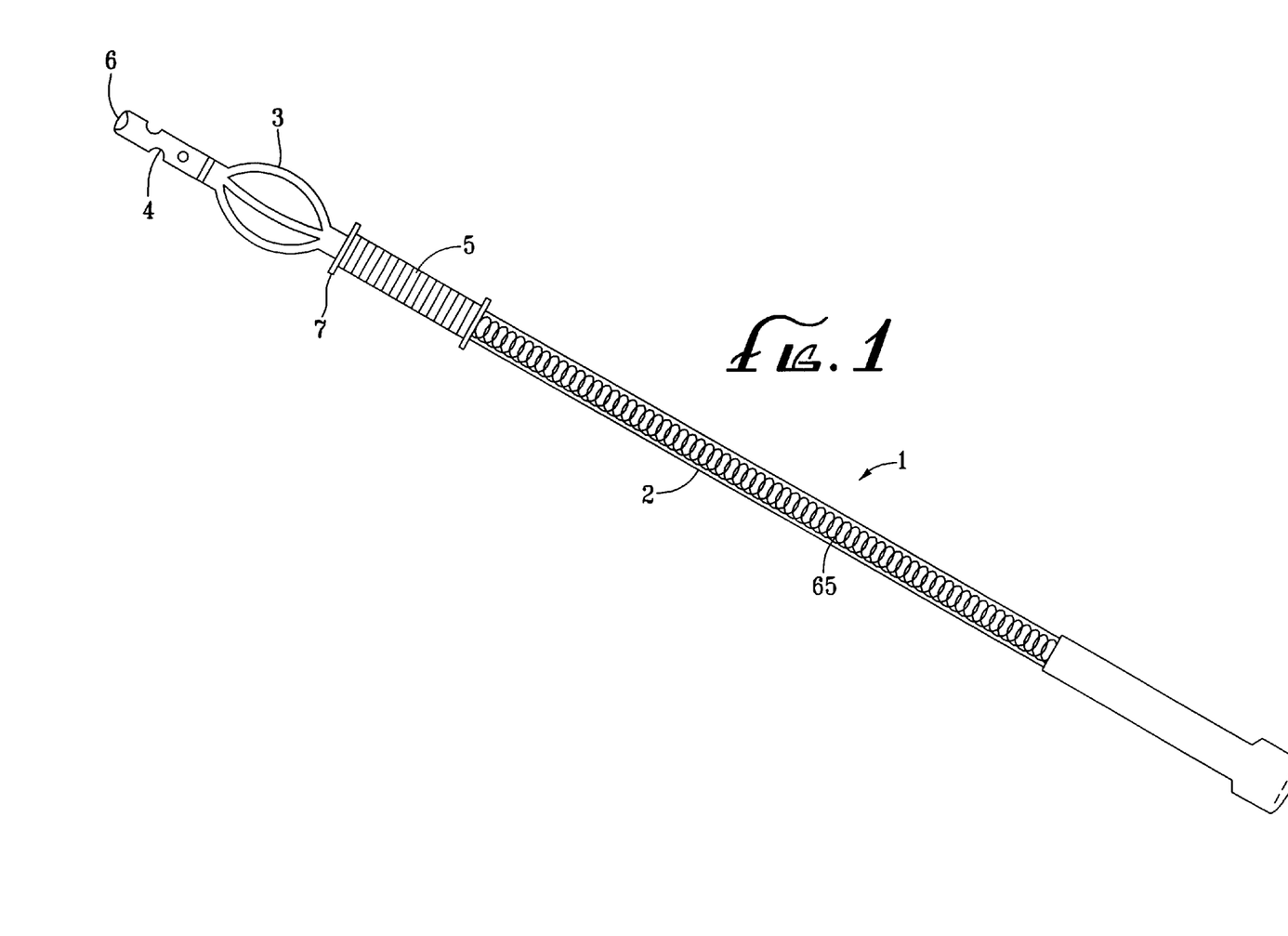
FIG. 1 depicts a longitudinal view of a venous drainage catheter.

A first embodiment of a venous drainage catheter is depicted in FIG. 1. Venous drainage catheter 1 is generally an elongated cylindrical element comprising cannula 2 having a proximal end, a distal end 6, and a lumen therebetween. Cannula 2 includes a plurality of drainage ports 4 disposed at the distal end of cannula 2. In certain embodiments, a single port will be adequate to withdraw blood at a sufficient rate for bypass. In other embodiments, two, three, four, five, or more ports may be necessary to accomplish cardiopulmonary bypass. The catheter may also include coil 65 to prevent kinking of the cannula, which may impede blood flow. Bellows 3 are arranged circumferentially proximal drainage ports 4, and provide fluid access to the cannula lumen. Cylindrical sheath 5 is disposed slidingly about cannula 2, sheath 5 further comprising a circumferential rib 7 in certain embodiments. Sheath 5 can be positioned to surround bellows 3, thereby radially compressing the bellows before deployment.

In use, the cannula shown in FIG. 1 is provided with sheath 5 disposed over bellows 3. An incision is made in the patient to provide access to the atrial appendage, typically by an intercostal route. Distal end 6 of cannula 2 is advanced through the incision and into the right atrium through the atrial appendage. As sheath 5 engages the incision at circumferential rib 7, cannula 2 is slid distally through sheath 5. Bellows 3 advances distally beyond sheath 5, thereby releasing the bellows as they enter the right atrium. Bellows 3 serves to maintain tissue in the right atrium spaced from drainage ports 4 sufficiently to provide unimpeded fluid access to drainage ports 4 and to the cannula lumen between the bellows. Expanding members 3 are thereby automatically actuated upon entry into the right atrium. The proximal end of cannula 2 is then attached to a bypass oxygenator machine and blood is withdrawn from the right atrium.

Figure 2:
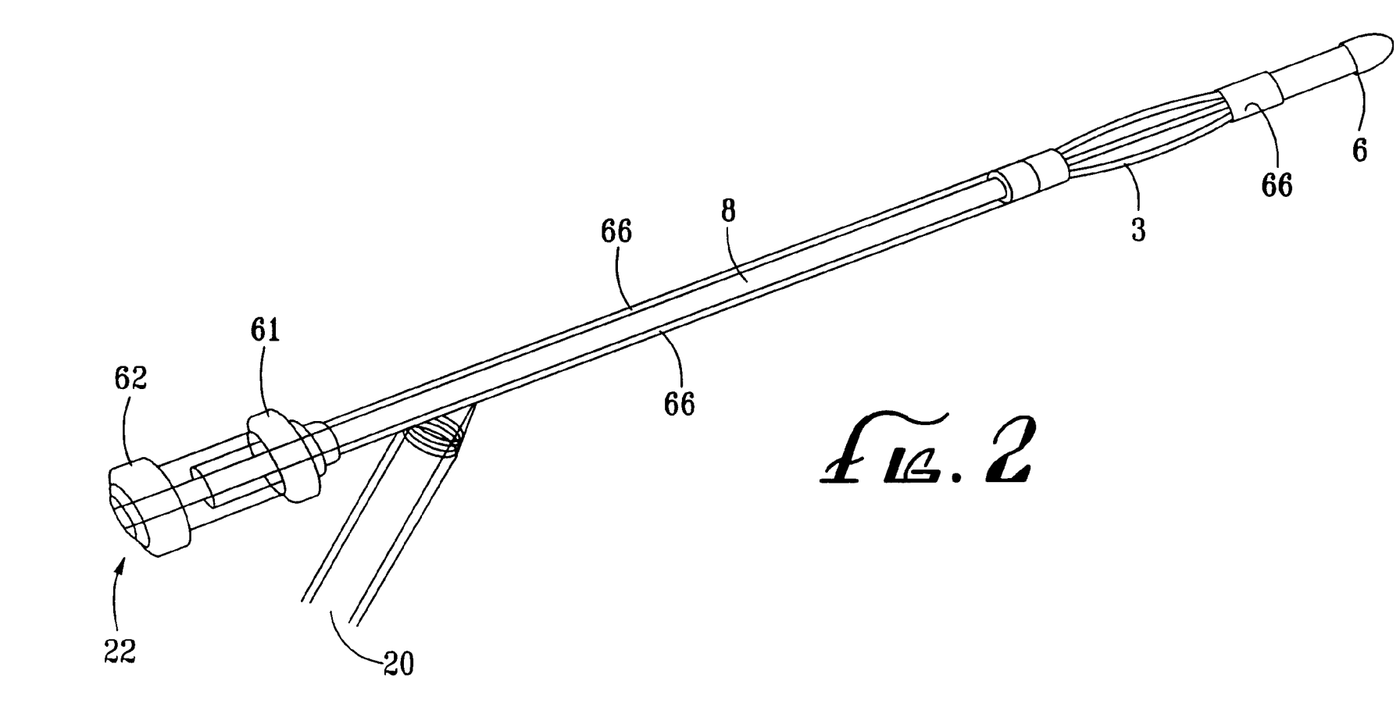
FIG. 2 depicts an alternative embodiment of a venous drainage catheter having arcuate handles at its proximal end.

In another embodiment, a venous drainage catheter is provided as depicted in FIG. 2. The catheter includes distal end 6, proximal end 22, and lumen 8. Distal end 6 includes at least one drainage port in fluid communication with lumen 8 of the catheter. An expanding member, shown here as bellows 3, may be disposed circumferentially about the drainage ports. Proximal end 22 includes arcuate handles 61 and 62, which are slidable relative to one another. Handle 61 may be joined to distal end 6 by one or more wires 66, while handle 62 is mounted to the proximal end of the catheter. Handle 61 and 62 are compressed during operation to retract distal end 6, thereby causing bellows 3 to expand radially outward. The proximal end of the catheter may also include a locking mechanism to lock handles 61 and 62 at a fixed displacement during use. The proximal end of the catheter further includes side port 20 which is adapted for attachment at its proximal end to a bypass-oxygenator machine. The lumen of port 20 merges and communicates distally with lumen 8 of the catheter, which lumen receives blood from the distal drainage port.

In use, the catheter has bellows 3 in a collapsed condition. An incision is made in the patient to provide access to the atrial appendage. Distal end 6 is inserted through the incision and into the right atrium. Handles 61 and 62 are compressed, thereby expanding bellows 3 radially outward to maintain tissue away from the drainage port and maintain fluid access to the drainage port. Deoxygenated blood is delivered from the right atrium through the drainage port and lumen 8 to a bypass-oxygenator machine through port 20.

Figure 3:
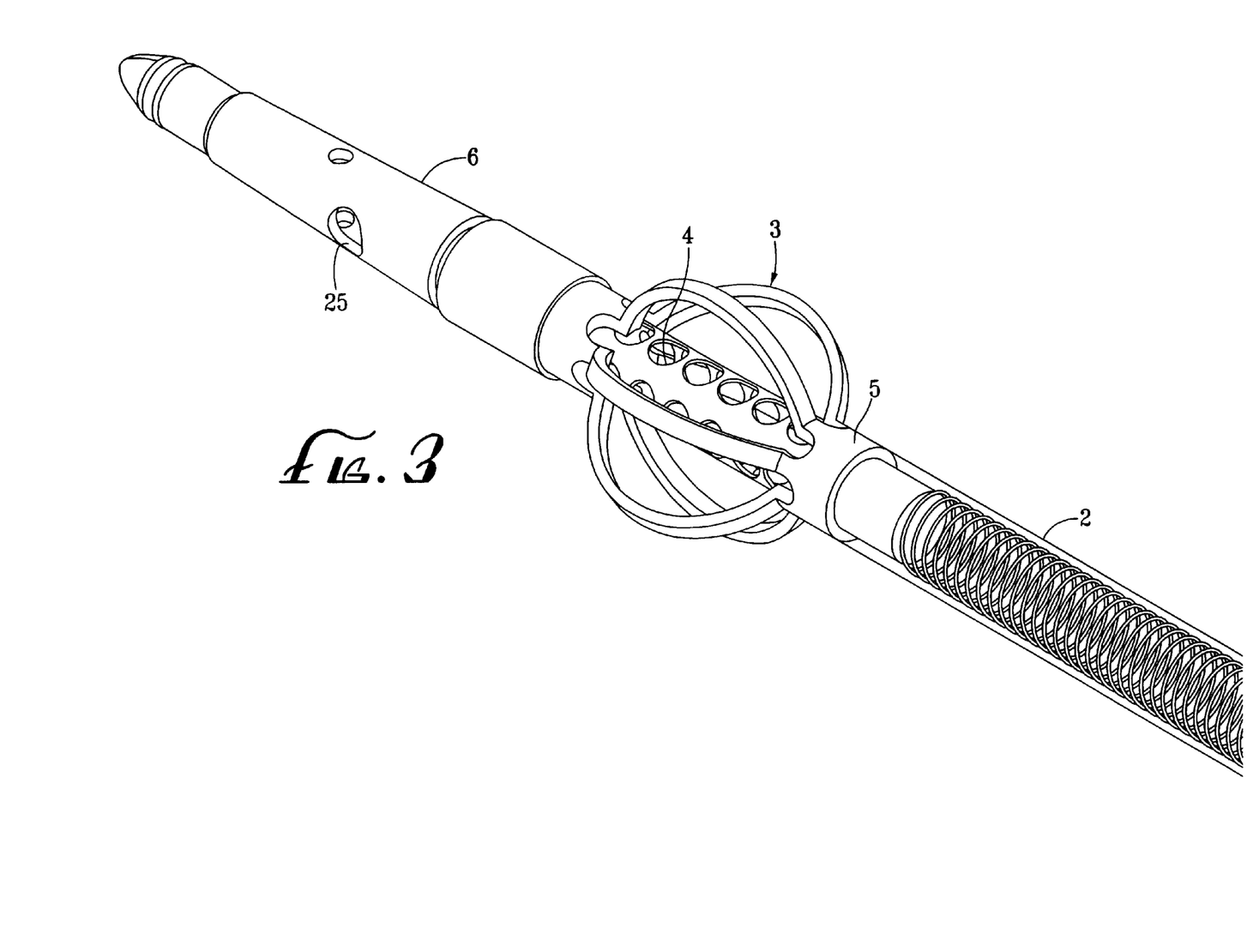
FIG. 3 depicts another alternative embodiment of a venous drainage catheter.

In another alternative embodiment depicted in FIG. 3, expanding members 3, shown here as bellows, are arranged circumferentially about drainage ports 4 of cannula 2. Cannula 2 further includes drainage port 25 at distal end 6. A cylindrical sheath (not shown) may be disposed slidably about cannula 2 to surround expanding members 3, thereby compressing the expanding member before deployment.

Figure 4:
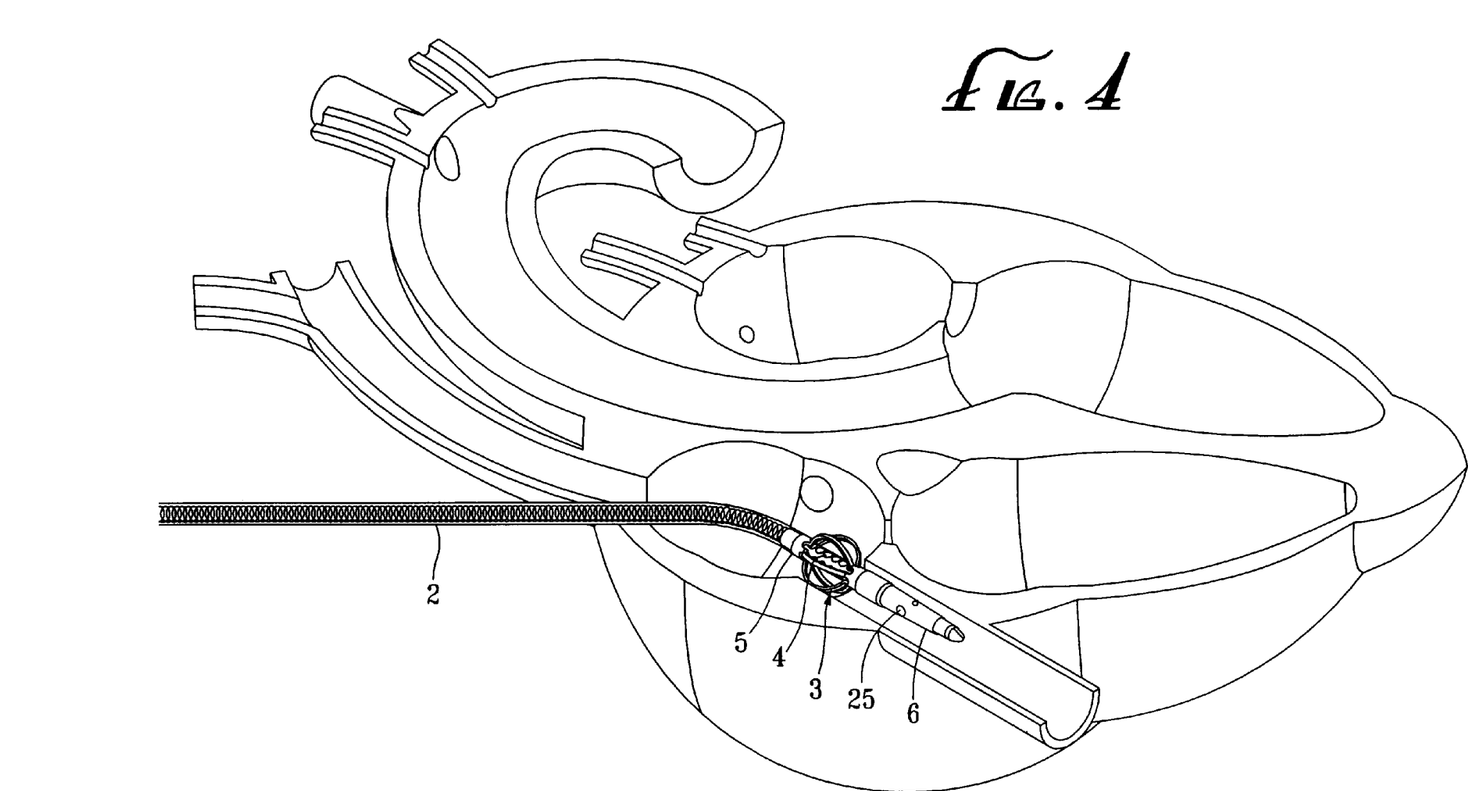
FIG. 4 depicts the venous drainage catheter of FIG. 3 deployed in the right atrium.

The venous drainage catheter of FIG. 3 is shown entering and deployed in the right atrium in FIG. 4. After an incision is made on the atrial appendage, distal end 6 of cannula 2 is advanced through the incision and into the right atrium, and expanding members 3 are decompressed and engaged in the opening of the inferior vena cava to the right atrium, holding atrial tissue away from drainage ports 4. Deoxygenated blood from the inferior vena cava and the right atrium can then enter through port 25 and ports 4, respectively, and be delivered to a bypass oxygenator machine.

Figure 5:
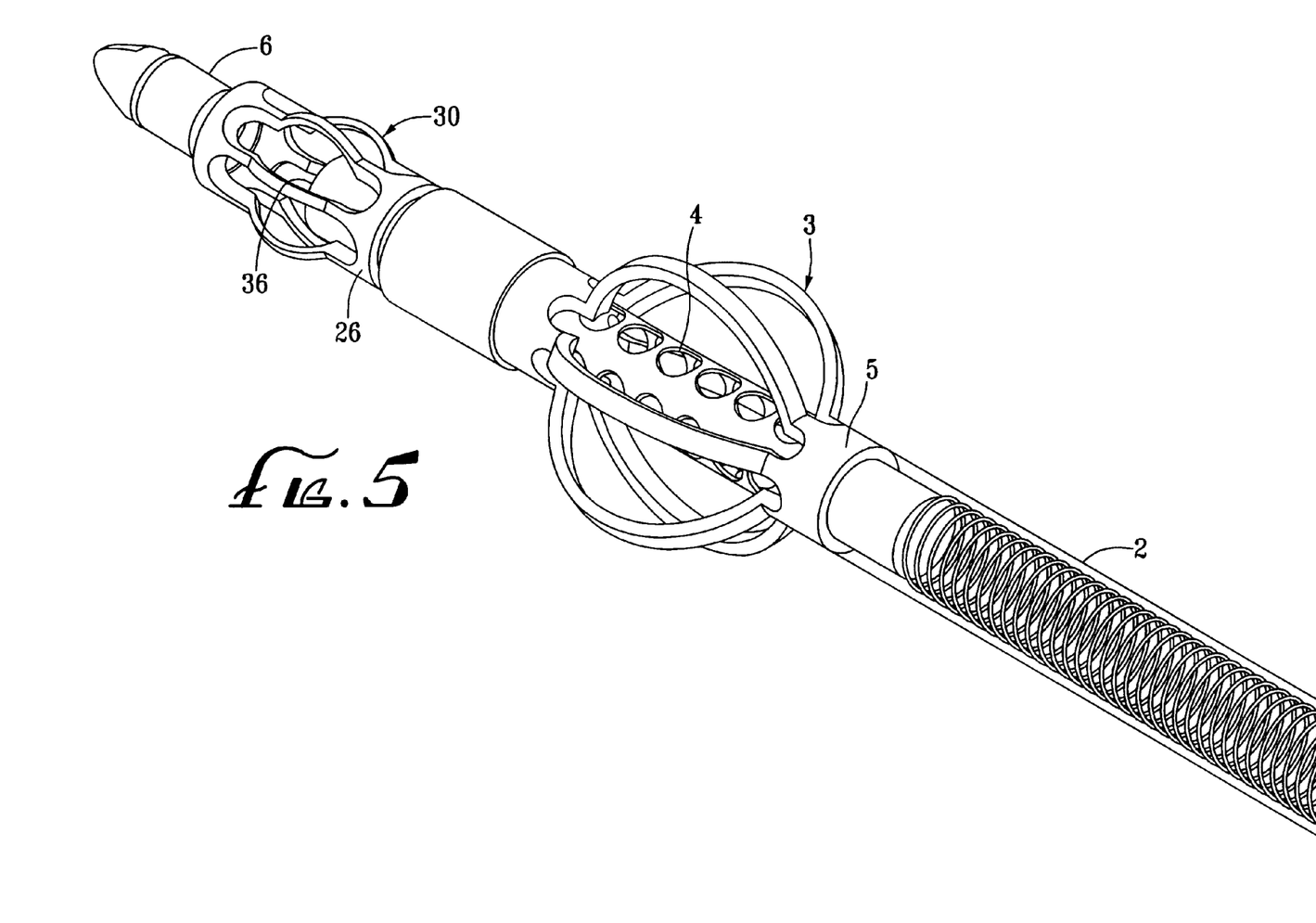
FIG. 5 depicts a venous drainage catheter having two expanding members at its distal end.

FIG. 5 depicts another embodiment of a venous drainage catheter having two expanding members. Cannula 2 has drainage port 36 at distal end 6 in addition to drainage ports 4. Expanding members 3 and 30, shown here as bellows, surround drainage ports 4 and drainage port 36, respectively. Cylindrical sheaths (not shown) may be disposed slidably about cannula 2. Such sheaths surround expanding members 3 and 36, thereby radially compressing both expanding members before deployment.

Figure 6:
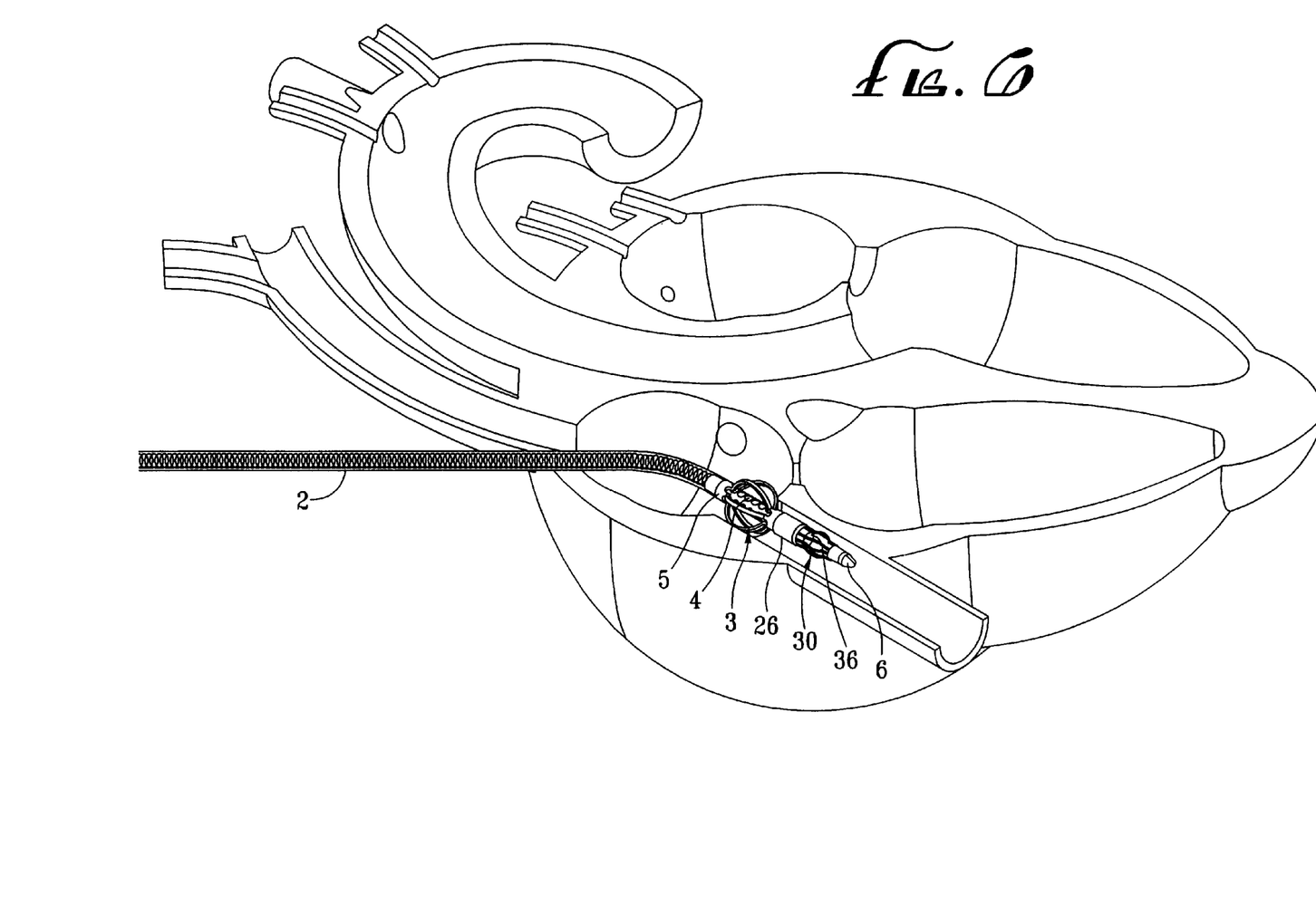
FIG. 6 depicts the venous drainage catheter of FIG. 5 deployed in the right atrium.

In FIG. 6, the venous drainage catheter of FIG. 5 is shown deployed in the right atrium. After an incision is made in the right atrial appendage by an access mechanism, the venous drainage catheter is inserted through the incision into the right atrium. A sheath (not shown) engages the incision, and cannula 2 is slid distally through the sheath, thereby releasing expanding member 3 by advancing the expanding members distally beyond the sheath. Distal end 6 of the venous drainage catheter is advanced into the inferior vena cava until expanding members 3 engage the opening of the inferior vena cava to the right atrium. In this way, expanding members 3 facilitate flow of the deoxygenated blood through drainage ports 4 from the right atrium, whereas expanding members 30 facilitate flow of deoxygenated blood through drainage port 36 from the inferior vena cava by keeping vascular tissue from collapsing on the drainage ports.

Figure 7:
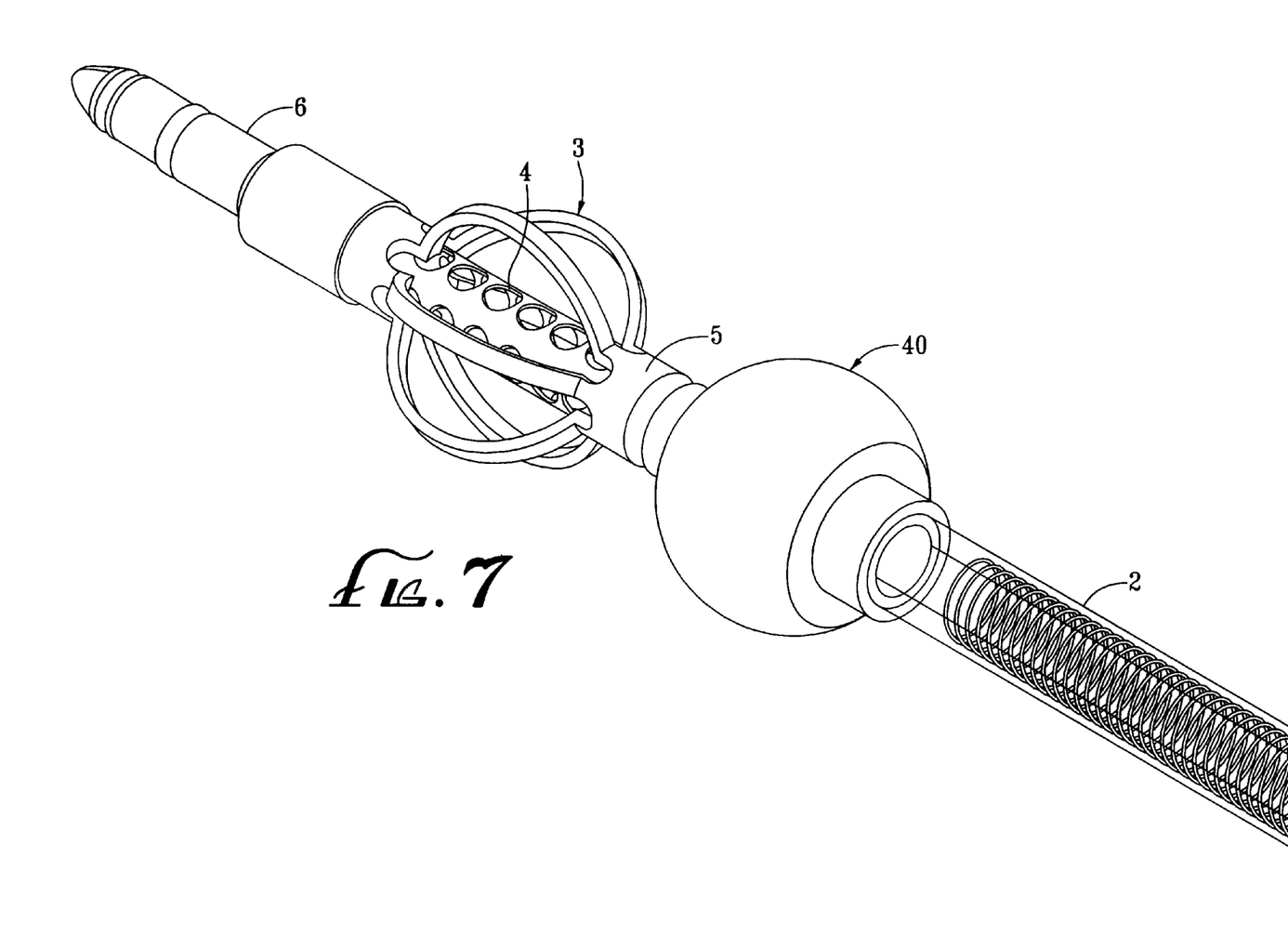
FIG. 7 depicts a venous drainage catheter having an expandable balloon at its distal region.

In FIG. 7, another alternative embodiment of a venous drainage catheter is shown having expandable balloon 40 mounted proximal to bellows 3. Drainage ports 4 again are surrounded by expanding members 3, shown here as bellows. A cylindrical sheath (not shown) may be disposed slidably about cannula 2 engaging bellows 3 before deployment. Expandable balloon 40 is sized to engage the openings of the inferior vena cava or superior vena cava into the right atrium.

Figure 8:
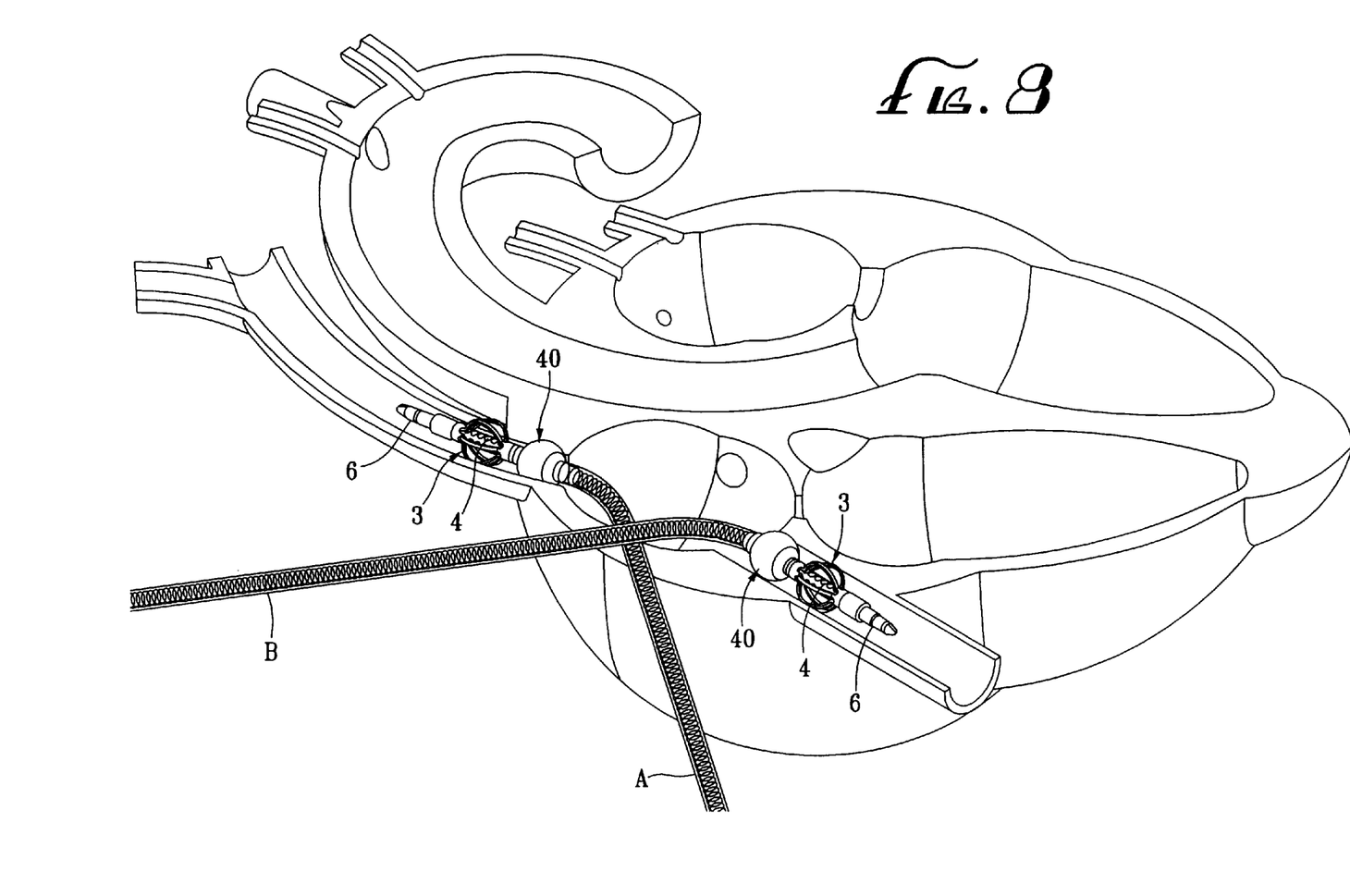
FIG. 8 depicts two venous drainage catheters of FIG. 7 deployed in the right atrium.

In FIG. 8, two venous drainage catheters are shown deployed within the right atrium. After an incision is made in the right atrial appendage, venous catheter A and venous catheter B are inserted through the incision into the right atrium. Expanding members 3 are released and expandable balloons 40 are inflated on both catheters. Catheter A is advanced in a cephalad direction to engage balloon 40 at the opening of superior vena cava into the right atrium. Catheter B is advanced in a caudal direction to engage balloon 40 at the opening of the inferior vena cava in to the right atrium. The balloons provide a seal at the atrial inlet, and thus facilitate venous drainage in the inferior vena cava and superior vena cava by minimizing runoff of deoxygenated blood into the right atrium. The expanding members further improve venous drainage by keeping the drainage ports open.

Figure 9:
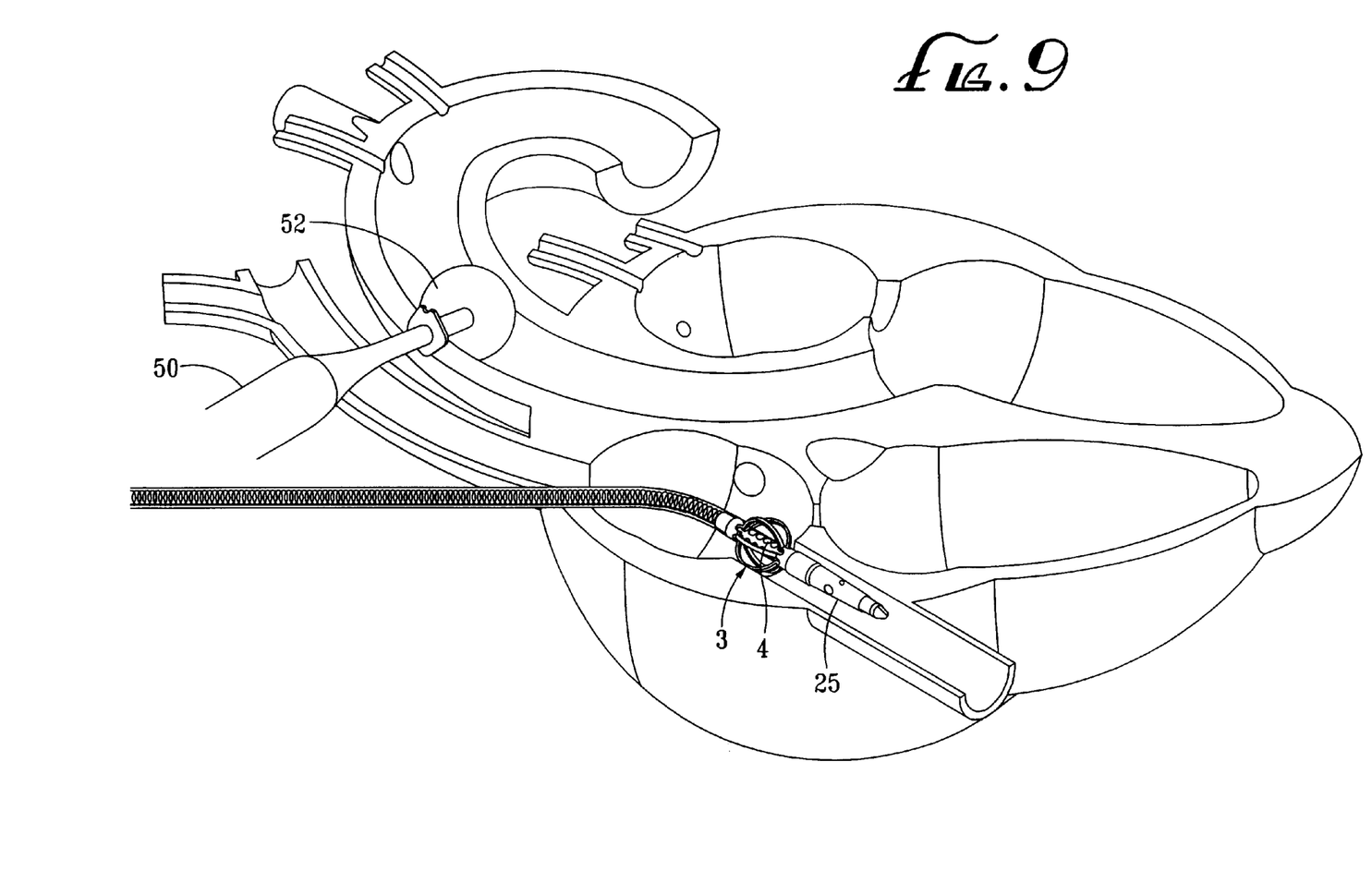
FIG. 9 depicts a venous drainage catheter deployed in the right atrium and an arterial cannula deployed in the aorta.

Arterial and venous cannulation are both required to initiate CPB. In FIG. 9, a venous drainage catheter 1 is deployed in the right atrial cannula whereas an arterial cannula 50 is deployed in the ascending aorta. Arterial cannula 50 includes expandable balloon 52 for occluding the aortic lumen. Venous drainage catheter 1 includes expandable member 3 (shown here as ribs) surrounding drainage ports 4 to prevent collapse of atrial tissue around the drainage ports. The venous drainage catheter drains venous blood from the inferior vena cava through port 25 and from the right atrium through ports 4, and delivers deoxygenated blood to an oxygenator bypass machine. The bypass machine then returns oxygenated blood to the ascending aorta through arterial cannula 50, thereby providing circulatory isolation of the heart and coronary blood vessels from the peripheral vascular system.

While particular devices and methods have been described for venous drainage catheters, once this description is known, it will be apparent to those of ordinary skill in the art that other embodiments and alternative steps are also possible without departing from the spirit and scope of the invention. Moreover, it will be apparent that certain features of each embodiment as well as features disclosed in each reference incorporated herein can be used in combination with devices illustrated in other embodiments. Accordingly, the above description should be construed as illustrative, and not in a limiting sense, the scope of the invention being defined by the following claims.

What is claimed is:

1. A method for draining venous blood from the right atrium of a patient, comprising the steps of:

providing a venous drainage catheter comprising a cannula having a drainage port at a distal end thereof, the drainage port in fluid communication with a lumen of the cannula, the cannula further having expanding members disposed about said drainage port and a cylindrical sheath disposed circumferentially about the expanding members;

making an incision in an atrial appendage of the patient to provide access to the right atrium;

inserting the cannula through the incision and into the right atrium, wherein the sheath is engaged by tissue surrounding the incision, and the expanding members slide beyond the sheath and into the right atrium, wherein the expanding members are released;

actuating the expanding members to an expanded condition to hold tissue away from the drainage port; and withdrawing venous blood from the right atrium.

2. The method of claim 1, further comprising the step of sealing the atrial appendage circumferentially around the cannula.

3. The method of claim 1, wherein the venous drainage catheter further comprises a proximal side opening which communicates with the lumen of the cannula, a second cannula slidably disposed within the lumen of the first cannula and passing through said side opening, the distal end of the second cannula having an opening aligned longitudinally with the drainage port of the cannula, and wherein the expanding members are carried by the housing first cannula.

4. The method of claim 3, wherein the step of inserting the cannula through the incision comprises the steps of:

inserting the first cannula through the incision and into the right atrium; and inserting the second cannula through the proximal side opening and through the lumen of the first cannula, and advancing the second cannula distally into the atrium until the drainage port of the first cannula aligns with the opening on the distal end of the second cannula.

\* \* \* \* \*

UNITED STATES PATENT AND TRADEMARK OFFICE
CERTIFICATE OF CORRECTION

PATENT NO. : 6,270,490 B1
DATED : August 7, 2001
INVENTOR(S) : Kevin Hahnen

Page 1 of 1

It is certified that error appears in the above-identified patent and that said Letters Patent is hereby corrected as shown below:

<u>Claim 3,</u>
Please delete [cannula, and wherein the expanding members are carried by the housing]

Signed and Sealed this

Sixteenth Day of April, 2002

Attest:

JAMES E. ROGAN
Director of the United States Patent and Trademark Office

Attesting Officer